United States Patent
Lean et al.

(10) Patent No.: US 7,150,813 B2
(45) Date of Patent: Dec. 19, 2006

(54) ISOELECTRIC FOCUSING (IEF) OF PROTEINS WITH SEQUENTIAL AND OPPOSITELY DIRECTED TRAVELING WAVES IN GEL ELECTROPHORESIS

(75) Inventors: Meng H. Lean, Santa Clara, CA (US); Huangpin Ben Hsieh, Mountain View, CA (US); John S. Fitch, Los Altos, CA (US); Armin R. Völkel, Mountain View, CA (US); Bryan Preas, Palo Alto, CA (US); Scott Elrod, La Honda, CA (US); Richard H. Bruce, Los Altos, CA (US); Eric Peeters, Fremont, CA (US); Frank Torres, San Jose, CA (US); Michael Chabinyc, Mountain View, CA (US)

(73) Assignee: Palo Alto Research Center Incorporated, Palo Alto, CA (US)

(*) Notice: Subject to any disclaimer, the term of this patent is extended or adjusted under 35 U.S.C. 154(b) by 434 days.

(21) Appl. No.: 10/460,724

(22) Filed: Jun. 12, 2003

(65) Prior Publication Data
US 2004/0251136 A1    Dec. 16, 2004

(51) Int. Cl.
*B01D 57/02* (2006.01)
(52) U.S. Cl. .............. 204/547; 204/643; 204/450; 204/600
(58) Field of Classification Search ............ 204/456, 204/459, 466, 548, 606, 610, 616, 644, 547, 204/643, 450, 600
See application file for complete search history.

(56) References Cited

U.S. PATENT DOCUMENTS

| | | | |
|---|---|---|---|
| 4,473,452 A | 9/1984 | Cantor et al. | |
| 4,647,179 A | 3/1987 | Schmidlin | |
| 4,737,251 A | 4/1988 | Carle et al. | |
| 4,900,414 A * | 2/1990 | Sibalis | 204/457 |
| 5,208,458 A | 5/1993 | Busch et al. | |
| 5,534,121 A | 7/1996 | Merrick et al. | |
| 5,653,859 A | 8/1997 | Parton et al. | |
| 5,837,116 A | 11/1998 | Harrington et al. | |
| 6,272,296 B1 | 8/2001 | Gartstein | |
| 6,296,752 B1 * | 10/2001 | McBride et al. | 204/547 |
| 6,358,752 B1 | 3/2002 | Durst et al. | |
| 6,398,933 B1 | 6/2002 | Scott | |
| 6,499,831 B1 | 12/2002 | Schmidlin | |
| 6,596,143 B1 * | 7/2003 | Wang et al. | 204/547 |
| 6,655,649 B1 * | 12/2003 | Panattoni | 249/97 |
| 6,881,314 B1 * | 4/2005 | Wang et al. | 204/600 |

(Continued)

FOREIGN PATENT DOCUMENTS

WO    WO 00/73780    12/2000

OTHER PUBLICATIONS

Scott Rudge et al., Electroseparations (Electrophoresis), *Encyclopedia of Chemical Technology*, 4th Edition, vol. 9, pp. 356-376.

(Continued)

*Primary Examiner*—Nam Nguyen
*Assistant Examiner*—Anthony Fick
(74) *Attorney, Agent, or Firm*—Fay, Sharpe, Fagan, Minnich & McKee, LLP (57) ABSTRACT

Various gel electrophoretic assemblies and techniques are disclosed for providing unique isoelectric focusing (IEF) strategies. Several particular systems, assemblies and methods are provided that significantly reduce processing time, enable the use of reduced operating voltages, and produce analytical results with improved resolution.

9 Claims, 5 Drawing Sheets

U.S. PATENT DOCUMENTS

2001/0023825 A1   9/2001   Frumin et al.
2002/0144895 A1   10/2002  Stern et al.

OTHER PUBLICATIONS

O'Hara et al., *Ratcheting Electrophoresis Microchip(REM)for Programmable Transport and Separation of Macromolecules*, MEMS, Nov. 11-16, 2001, pp. 619-628, vol. 3, ASME, USA.

Dunphy et al., *Rapid Separation and Manipulation of DNA by a Ratcheting Electrophoresis Microchip(REM)*, Nov. 17-22, 2002, pp. 419-423, ASME, USA.

Proteome Systems, Products, Website, E*lectrophoretIQ³*, 2002 at http://www.proteomesystems.com/product/product.asp-?ProductID=43 and http://www.proteomesystems.com/product/profile.asp?DocumentID=662.

ISC Buyer's Guide, Website, *Electrophoresis, 2D Gel*, 2002, at http://www.iscpubs.com/bg/us/prod/prod1991.html.

EMBL's Proteomics Visitor Facility, Website, 2D Gel Equipment, *Protean 2D Cells from Bio-Rad*, 2001, at http://mann.embl-heidelberg.de/Visitor_Facility/PageLinks/Instrumentation/GelchamberMain.html, and *Protean IEF Cell from Bio-Rad*, at http://www.mann.embl-heidelberg.de/Visitor_Facility/PageLinks/Instrumentation/ECellMain.html.

James R. Jefferies, *2D Gel Electrophoresis for Proteomics Tutorial*, pp. 1-24 at http://www.aber.ac.uk/parasitology/Proteome/Tut_2D.html (last tutorial update: Jan. 7, 2003).

The Scripps Research Institute, Website, *Proteomics Module*, 2003, pp. 1-3 at http://core-eye.scripps.edu/proteomics.htm.

2D Protocols, Website, *Analysis of Proteins Using Small Format 2D Gel Electrophoresis*, 2000, pp. 1-5, at http://www.abdn.ac.uk/~mmb023/protocol.htm.

Biowire.com, Website, *The Nucleus*, 2000-2002, pp. 1-4, at http://www.biowire.com/nucleus/nucleus_1_3.jsp.

Bio-Rad Laboratories, Website, *Electrophoresis*, 2003, at http:www.bio-rad.com/B2B/BioRad/produict/br_category.jsp.

Bjellqvistb et al: "Isoelectric Focusing in Immobilized PH Gradients: Principle, Methodology and Some Applications," Journal of Biochemical and Biophysical Methods, Amsterdam, NL, vol. 6, 1982, pp. 317-339.

Hagedorn R et al: "Traveling-Wave Dielectrophoresis of Microparticles," Electrophoresis, Weinheim, DE, vol. 13, No. 1/2, Jan. 1992, pp. 49-54.

* cited by examiner

ISOELECTRIC FOCUSING (IEF) OF PROTEINS WITH SEQUENTIAL AND OPPOSITELY DIRECTED TRAVELING WAVES IN GEL ELECTROPHORESIS

TECHNICAL FIELD

The present invention relates to the field of electrophoretic separation of molecules, and, more particularly, to isoelectric focusing. The present invention also relates to analytical methods based upon the observation of the migration of particles in response to an electric field.

BACKGROUND OF THE INVENTION

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by molecular size.

One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches an isoelectric point and is thereafter immobile in the electric field. Therefore, this electrophoresis procedure separates molecules according to their different isoelectric points.

More specifically, this procedure is referred to as isoelectric focusing (IEF) wherein an electric field is applied to a molecule in a pH gradient to mobilize the molecule to a position in the pH gradient at which its net charge is zero, i.e., the isoelectric point of the molecule. It often is used to separate proteins in a mixture and as an aid in the characterization of biomolecules of unknown composition. Commercially available gradients maybe utilized in isoelectric focusing which consist of multicharged ampholytes, with closely spaced isoelectric values and high conductivity, which partition into a pH gradient upon application of an electric field. The ampholytes are generally provided in a support matrix, such as a polyacrylamide gel.

Because protein samples are actually ampholytes, when samples are loaded onto the gel and a current is applied, the compounds migrate through the gel until they come to their isoelectric point where they reach a steady state. Isoelectric focusing takes a long time (from about 3 to 30 hours) to complete because sample compounds move more and more slowly as they approach the pH in the gel that corresponds to their isoelectric points. Because the gradient ampholytes and the samples stop where they have no mobility, the resistivity of the system increases dramatically toward the end of the experiment, and the current decreases dramatically. For this reason, isoelectric focusing is usually run with constant voltage. Constant current application can lead to overheating of the system.

The combination of sodium dodecyl sulfate (SDS), $CH_3(CH_2)_{10}CH_2OSO_3Na$, also known as lauryl sulfate, treatment of samples and polyacrylamide gel electrophoresis was first described in the late 1960's. SDS is an ionic surfactant which solubilizes and denatures proteins. The surfactant coats a protein through hydrophobic interactions with the polypeptide backbone, effectively separating most proteins into their polypeptide subunits. The majority of proteins to which SDS binds then unfold into linear molecules having a similar surface potential.

SDS-polyacrylamide gel electrophoresis (SDS-PAGE) allows separation of molecules strictly on the basis of size, i.e., molecular weight. When SDS-treated samples migrate into a gel and are electrophoresed, the principal difference is size or length. Smaller molecules travel through the matrix more quickly than those that are larger. The rate at which molecules migrate through a polyacrylamide gel is inversely linear with the logarithm of their molecular weight. Thus denatured samples can be analyzed alongside standards of known molecular weight to aid in the interpretation of a substance's physical size.

Two-dimensional (2D) electrophoresis is unique, offering an analytical method that is both reproducible and sensitive. It is referred to as 2D because it employs two different methods of electrophoresis, in two different dimensions, to produce one result. Each method separates the sample compounds based on different properties of each compound. The combination of the two methods gives better resolution of the compounds in the sample than could be achieved with either method alone. For example, each method alone may separate up to 100 components of a sample, whereas together they may separate up to 10,000 components.

A pair of electrophoretic techniques commonly employed in 2D analyses are the previously noted isoelectric focusing (IEF) and SDS-polyacrylamide gel electrophoresis (SDS-PAGE). IEF separates sample compounds according to isoelectric point, whereas SDS-PAGE separates the compounds by molecular weight. A 2D analytical technique using IEF and SDS-PAGE to separate total protein results in a gel having bands or spots in a random pattern. Each spot represents a unique component of a sample. A single charge difference in a component can be identified on the gel by a unique spot. This property of 2D electrophoresis, which allows identification of identical proteins that differ by one charge difference, has made it an invaluable technique for the molecular genetic community.

As noted, many proteins are separated by polyacrylamide gel electrophoresis (PAGE) (based on the molecular weight) or modified polyacrylamide gel isoelectric focusing (IEF) (based on molecular charge). Both of the techniques can be used in tandem in a two-dimensional approach for maximum resolution. Polyacrylamide gels are made by polymerizing the monomer, acrylamide, into long strands, and then linking the strands together with a 'cross-linker', usually N,N'-methylene-bis-acrylamide (bis). The relative proportions of these components will determine the separation characteristics of the gel. Isoelectric focusing is carried out in a PAGE gel that contains an immobilized pH gradient consisting of high molecular weight polyaminocarboxylic acid (ampholytes). The separation power of two dimensional polyacrylamide gel electrophoresis (2D PAGE) has often been exploited as part of isolation schemes for determining the amino acid sequence of unknown proteins from complex protein mixtures.

Particles can be manipulated by subjecting them to traveling electric fields. Such traveling fields are produced by applying appropriate voltages to microelectrode arrays of suitable design. Travelling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarisable particle in a non-uniform electric field. Essentially, the force arises from the interaction of the field non-uniformity with a field induced charge redistribution in the separated particle.

Particles are manipulated using non uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Travelling Wave Field Migration was described by Parton et al. in U.S. Pat. No. 5,653,859, herein incorporated by reference. Although satisfactory, this work is not directed to the field of protein analyses and in particular, to isoelectric focusing or 2D gel electrophoresis techniques utilizing an isoelectric focusing step.

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17–22, 2002 New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory proteomic equipment. Moreover, the strategy described by Dunphy et al. is silent with regard to applications involving 2D gel electrophoretic techniques, and more significantly, to IEF. Accordingly, a need exists for a device and technique for utilizing electrostatic traveling waves in conjunction with IEF and 2D gel electrophoresis techniques and equipment utilizing an IEF step.

Two-dimensional (2D) gel electrophoresis, particularly, such technique using an IEF step, is the acknowledged workhorse for proteomic research because it is simple, has high capacity, and is able to identify all proteins resolved on the gel when coupled with a mass spectrometer. However, lengthy process time, difficulty in resolving low-abundance proteins, and poor reproducibility, among other factors, has limited its full potential to becoming the definitive tool for proteomics. Specifically, conventional IEF processes require relatively long time periods and very high operating voltages. The present invention addresses the IEF step of 2D techniques, and provides a new instrument design and technique to reduce processing time, utilize lower operating voltages, and increase resolution by reducing band broadening with electrostatic traveling waves (TW).

BRIEF DESCRIPTION OF THE INVENTION

The present invention utilizes electrophoretic force arising from electrostatic traveling waves having an opposite polarity from the biomolecules undergoing separation. The traveling waves are administered in sequential sweeps across electrode grids to move the biomolecules to a location in an electrophoretic gel corresponding to their isoelectric point. In addition, the use of particular electrical grids through which the traveling waves pass, produces relatively strong electrical fields thereby requiring relatively low operating voltages.

In a first aspect, the present invention provides a gel electrophoretic system for separating biomolecules according to their isoelectric point. The system comprises an electrophoretic cell having two opposite ends and a gel medium extending between the ends. The gel medium provides a pH gradient along a length dimension between the ends. The system also comprises an electrode grid disposed in close proximity to the gel which includes a plurality of closely spaced parallel electrodes. The grid is oriented with respect to the cell such that the electrodes extend in a direction generally perpendicular to the length dimension of the cell. The system also comprises a voltage controller that provides a multi-phase electrical signal. The signal is either a positive traveling wave signal or a negative traveling wave signal. The controller is in electrical communication with the electrode grid such that the traveling wave signal passes from a first region of the electrode grid to a second region of the electrode grid.

In another aspect, the present invention provides a gel electrophoretic system for decreasing the time required for conducting isoelectric focusing of a sample of biomolecules. This system comprises an immobilized pH gradient (IPG) strip having a medium with pH increasing along a longitudinal axis of the strip. The system also comprises an electrode grid disposed adjacent to the strip. The electrode grid includes a plurality of parallel electrodes. The electrodes extend in a direction generally transverse to the longitudinal axis of the strip. The system further comprises a voltage controller providing a multi-phase electrical signal in the form of either a positive traveling wave signal or a negative traveling wave signal. The voltage controller is in electrical communication with the electrode grid such that the traveling wave signal travels from a first region of the electrode grid to a second region of the electrode grid.

In yet another aspect, the present invention provides a process for moving a biomolecule from a first location to a second location in an electrophoretic cell of a gel electrophoretic system. The system includes the electrophoretic cell having a medium providing a pH gradient along an axis of the cell. The system also includes an electrode grid disposed in close proximity to the cell. The grid includes a plurality of closely spaced parallel electrodes. The grid is oriented with respect to the cell such that the electrodes extend at right angles to the axis of the cell. The system also includes a voltage controller that provides a multi-phase electrical signal. The controller is in electrical communication with the electrode grid. The process comprises a first step of depositing the biomolecule or sample containing such, at a first location on the electrophoretic cell. The process additionally includes a step of providing the multi-phase electrical signal to a first region of the electrode grid. The signal passes the biomolecule on the cell as the signal travels from a first region of the grid to a second region of the grid. This moves the biomolecule from the first location on the cell to, or toward, a second location on the cell.

In yet a further aspect, the present invention provides a process for focusing at least two bands of biomolecules on an immobilized pH gradient (IPG) strip in an electrophoretic system. The system includes an electrode grid positioned in close proximity to the strip. The grid has a plurality of closely spaced parallel electrodes. The grid is oriented with respect to the cell such that the electrodes extend generally perpendicular to the strip. The system also includes a first voltage controller adapted to provide a first multi-phase electrical signal. The first controller is in electrical communication with at least a portion of the grid. The system also includes a second voltage controller adapted to provide a second multi-phase electrical signal. The second controller is in electrical communication with at least another portion of the grid. The process comprises a step of identifying the native charge of biomolecules in a first band disposed closest to a first end of the strip. The process includes another step of identifying the native charge of biomolecules in a second band disposed closest to a second end of the strip. The process includes a step of operating the first voltage controller to generate the first multi-phase electrical signal and cause the signal to pass from the first end of the strip toward the second end of the strip. The first signal has a polarity opposite from the native charge of the biomolecules in the first band. The process includes another step of operating the second voltage controller to generate a second multi-phase electrical signal and cause that signal to pass from the second end of the strip toward the first end of the strip. The second signal has a polarity opposite from the native charge of the biomolecules in the second band.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Separation and identification of biomolecules such as proteins and DNA is an important step in biotechnology. In this post-genomic period, 2D gel electrophoresis is emerging as the workhorse for protein separation. The methodology is 30 years old and has seen mostly minor technology improvements. The present invention provides an apparatus and a method to accelerate an IEF process or the IEF stage of a 2D process using such stage, by using electrostatic traveling waves having a particular polarity and directionality to selectively move or induce migration of both positive and negative proteins, biomolecules, or components thereof, in an electrophoretic gel system.

The primary objective of using electrostatic traveling waves is the very rapid transport of biomolecules to be separated in a gel electrophoretic cell. This rapid transport is achieved by creating very high local electrical fields with low voltages using an electrode grid with a very fine pitch that is positioned in close proximity to the electrophoretic cell. Pitch is a characteristic of the grid dimensions and is the distance between electrode centers. The present invention provides several advantages over conventional gel setups including lower voltages (1V as compared to 200V for PAGE and 8,000 V for conventional IEF), and much higher transport velocities (up to 10 times or more). However, band broadening tends to occur due to the characteristic trait of this mode of transport. In order to counter or reduce band broadening, the methods of the present invention ensure that the biomolecules are loaded onto the analyzing cell, i.e. an immobilized pH gradient (IPG) strip, such that they are within reach of the electrical fields from the traveling wave grid. After several cycles of the traveling wave signal, the biomolecules synchronize their motion to move in step to the sweep frequency of the traveling wave signal. Once synchronized, the propagation velocity of the biomolecules in the operating regime of interest is approximately a linear function of the sweep frequency.

Unless all biomolecules are completely loaded at any given time, the remnants contribute to band broadening as they are transported in succeeding traveling wave cycles. Near their isoelectric point, biomolecules such as proteins take much longer to converge with traditional linear electrical fields. It is contemplated that the preferred back and forth sweep of the two traveling waves employed in the strategy of the present invention accelerates the convergence and also the focusing of the band. These aspects are described in greater detail herein.

Figure 1A:
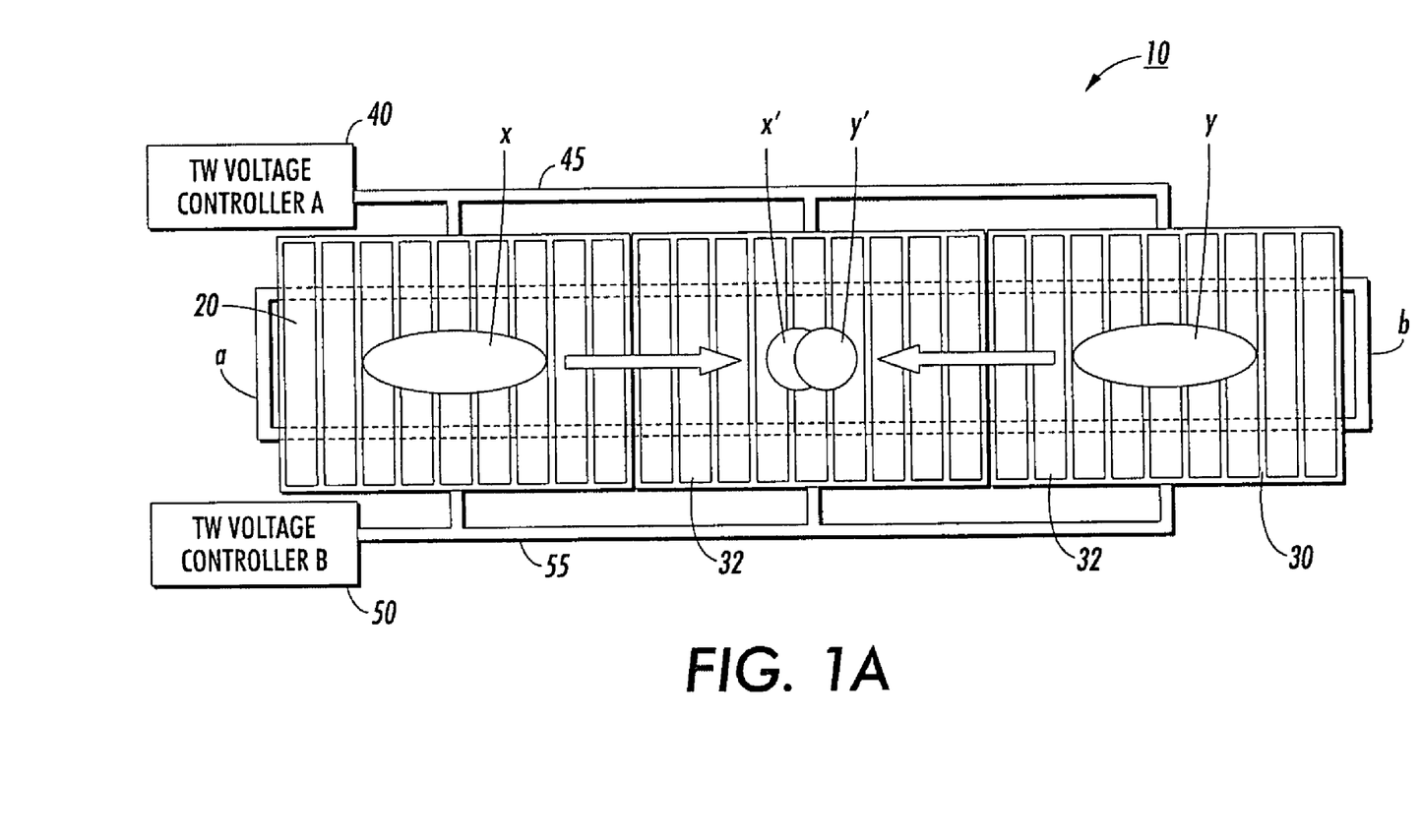
FIG. 1A is a schematic illustration of a preferred embodiment gel electrophoretic system in accordance with the present invention.

Currently known IEF techniques require a relatively long time and require very high operating voltages. In the present invention, traveling wave patterns of opposite polarity from the biomolecules being separated, such as proteins, are used in sequential sweeps to move the proteins to their respective isoelectric points. FIG. 1A is a schematic view of a preferred embodiment gel electrophoretic system 10 in accordance with the present invention. The system 10 includes an immobilized pH gradient (IPG) strip 20 and a multi-segmented traveling wave grid 30. The grid 30 includes a plurality of relatively fine and closely spaced parallel electrodes 32. The strip 20 is preferably oriented with respect to the grid 30 such that each electrode 32 extends in a direction that is generally perpendicular to the length dimension of the cell 20. The grid 30 is preferably a collection of individual grid segments that are in electrical communication to provide a single continuous grid. It will be appreciated, however, that in accordance with the present invention one or more grid segments may be selectively tailored or reconfigured with respect to the other grid segments. The preferred system 10 further includes a first traveling wave voltage controller 40, designated as controller A, and a second traveling wave voltage controller 50, designated as controller B. Each of the controllers 40 and 50 are in electrical communication with the grid 30 by corresponding busses 45 and 55, respectively. Disposed on the strip 20 is a first sample of biomolecules x and a second sample of biomolecules y. The biomolecules x have a positive native charge and the biomolecules y have a negative native charge. It will be appreciated that the first and second samples may be bands, patches, or remnants of biomolecules such as proteins that have already undergone separation or migration in the gel.

In accordance with the present invention, upon application of a negative electrical traveling wave directed towards side b of the strip 20, the biomolecules x migrate to a new position x'. That new position x' is closer to the location on the strip 20, and specifically within the gel medium therein, corresponding to the isoelectric point of biomolecule x. Ideally, that new position x' corresponds to the isoelectric point of biomolecule. Similarly, biomolecules y, having a negative native charge, are urged or directed towards side a of the strip 20 upon application of a positive electrical traveling wave directed towards side a of strip 20.

Figure 1B:
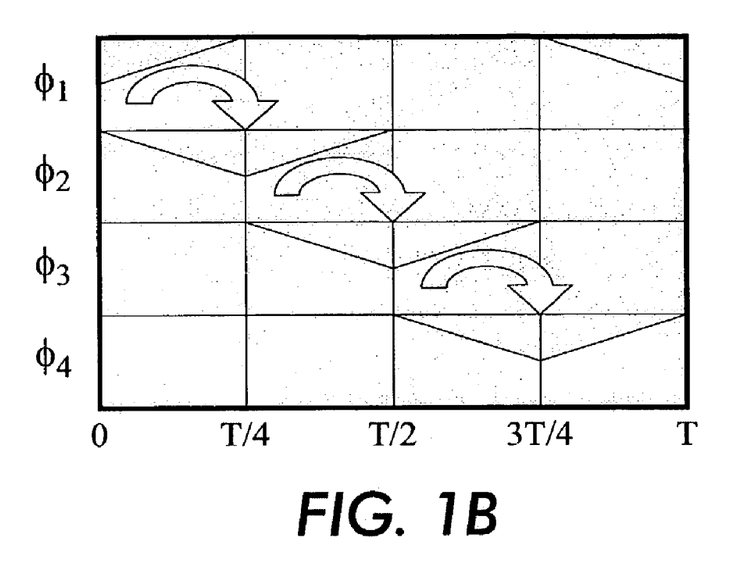
FIG. 1B is a wave diagram of a first set of electrical traveling waves utilized in the system of FIG. 1A.

More specifically, FIG. 1B illustrates a negative electrical traveling wave directed to side b of the strip 20 by controller 40. The controller 40 preferably generates a four (4) phase traveling wave in the form shown in FIG. 1B, which travels toward side b of the strip 20. As previously noted, the negative traveling wave causes migration of biomolecules x having a positive charge also toward side b of the strip 20. The biomolecules x will travel in such direction to a location on the strip 20 corresponding to their isoelectric point, i.e. shown as x' in FIG. 1A.

Figure 1C:
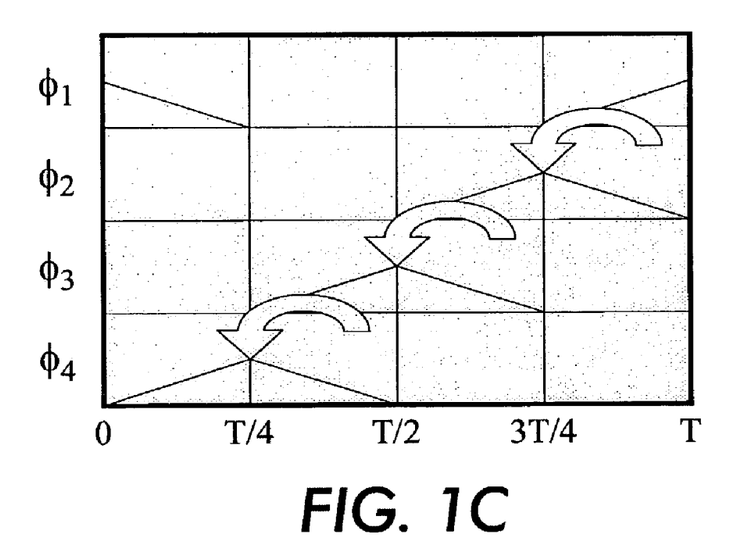
FIG. 1C is a wave diagram of a second set of electrical traveling waves utilized in the system of FIG. 1A.

Similarly, FIG. 1C illustrates a positive traveling wave directed to side a of the strip 20 by controller 50. The controller 50 preferably generates a four (4) phase traveling wave in the form shown in FIG. 1C, which travels toward side a of the strip 20. As previously noted, the positive traveling wave causes migration of biomolecules y having a negative charge toward side a of the strip 20. The biomolecules y will travel in such direction to a location on the strip 20 corresponding to their isoelectric point, i.e. shown as y' in FIG. 1A.

The electrical signal generated by the controller is referred to as a traveling wave because the same change in voltage, i.e. the "valley" or negative voltage change in each phase of the wave diagram of FIG. 1B or the "peak" or positive voltage change in each phase of the wave diagram of FIG. 1C, "travels" from one phase to another as a function of time. Thus, by providing electrical communication between the respective phases and sets of electrodes of a grid, the voltage changes, i.e. the peaks or valleys, can be made to travel across the electrode sets and thus, across the grid. Therefore, a traveling wave of the desired type, i.e. either a positive or negative wave, maybe directed from any desired region of the grid, to any other desired region.

The sets of traveling waves from controllers 40 and 50, i.e. shown in FIGS. 1B and 1C, are alternately applied to the grid 30. This alternating application of the sets of traveling waves causes progressive migration of biomolecules, i.e. biomolecules x and y, toward the corresponding isoelectric points of those biomolecules, or at least toward the center of the strip 20 and grid 30. This "focusing" effect reduces band broadening that otherwise typically occurs during IEF procedures.

A preferred technique utilizing the system depicted in FIG. 1A is to selectively alternate applications of the two controller signals to progressively migrate and focus the biomolecules. Controller 40 is arbitrarily selected to initially produce the desired voltage pattern, such as shown in FIG. 1B, for an appropriate time interval equivalent to some integral number of cycles. Traveling waves of the pattern of FIG. 1B are directed toward side b for a number of cycles. This number is generally the minimum number of cycles necessary for the biomolecules to synchronize their motion with the traveling wave signal. Then, controller 50 is selected to produce or sweep traveling waves of the pattern of FIG. 1C toward side a for the same number of cycles. At any given time, only one set of voltage pulses is applied to the grid 30. This method doubles the time needed but the rapid transport velocity of the biomolecules makes such method viable and attractive.

Figure 2A:
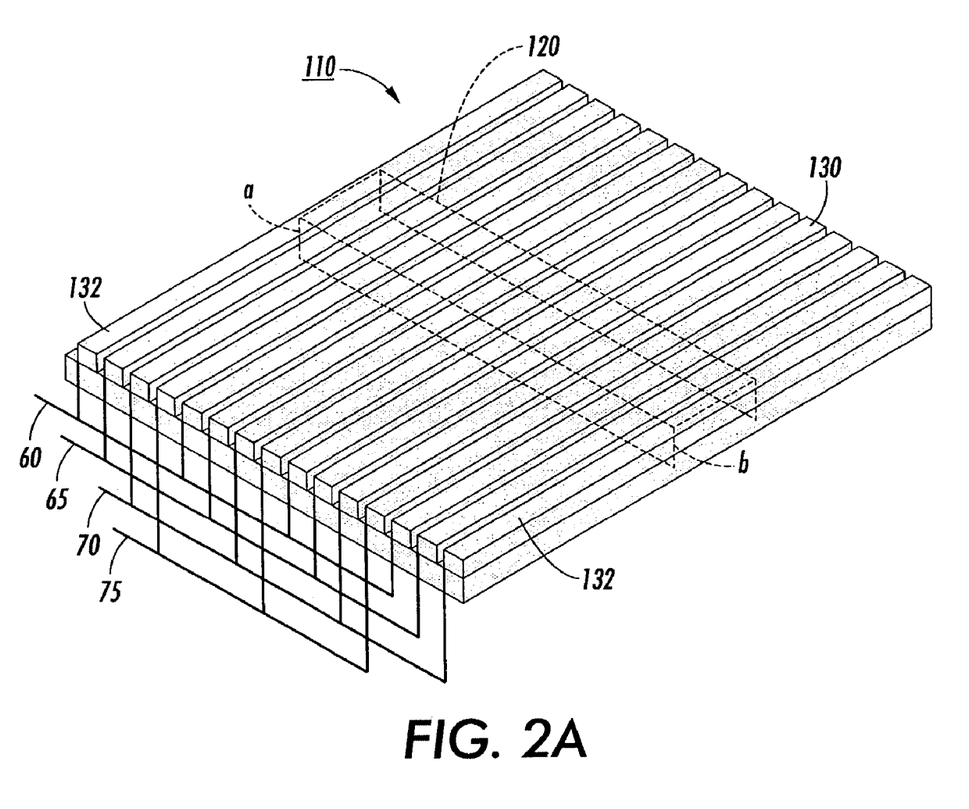
FIG. 2A is a schematic illustration of another preferred embodiment gel electrophoretic system in accordance with the present invention.

FIG. 2A illustrates another preferred embodiment gel electrophoretic system 110 in accordance with the present invention. The system 110 includes an IPG strip 120 disposed in intimate proximity to a traveling wave grid 130. The strip 120 has a first end a and a second end b, opposite from end a. The grid 130 includes a plurality of relatively fine and closely spaced parallel electrodes 132. The grid 130 is in electrical communication with a plurality of electrical busses, such as busses 60, 65, 70, and 75. The strip 120 is preferably oriented with respect to the grid 130 such that each electrode 132 extends in a direction that is generally perpendicular to the length dimension of the strip 120.

Figure 2B:
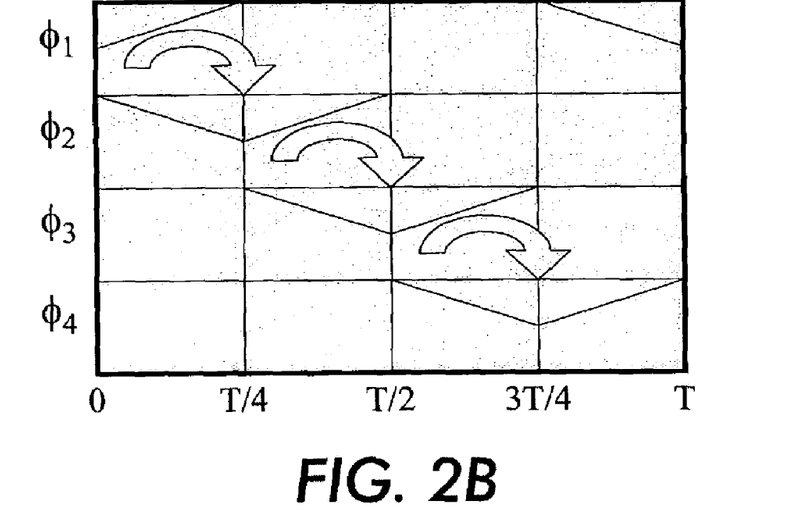
FIG. 2B is a wave diagram of a first set of electrical traveling waves utilized in the system of FIG. 2A.
Figure 2C:
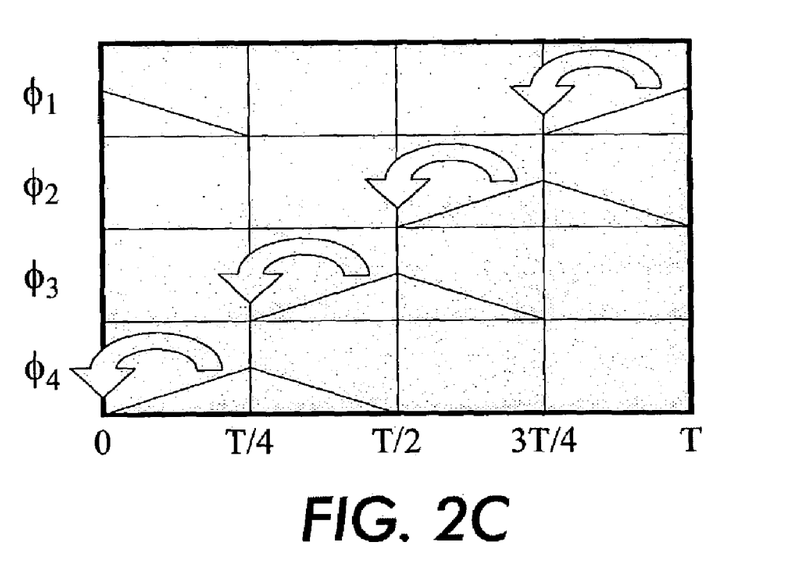
FIG. 2C is a wave diagram of a second set of electrical traveling waves utilized in the system of FIG. 2A.

FIG. 2B illustrates a negative electrical traveling wave directed to side b of the strip 120. The wave is preferably a four (4) phase traveling wave in the form shown in FIG. 2B. FIG. 2C illustrates a positive traveling wave directed to the other side of the strip 120, i.e. side a.

Figure 2D:
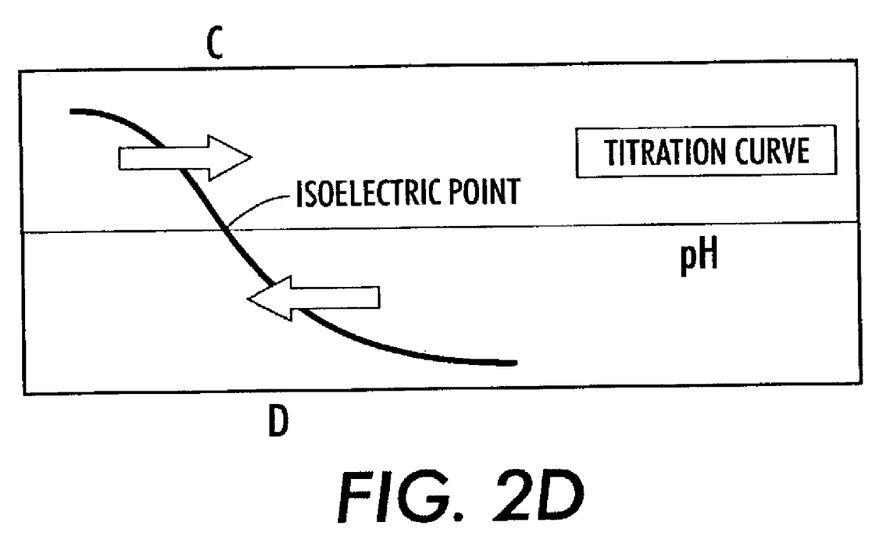
FIG. 2D is a representative titration curve illustrating an aspect of the present invention.

FIG. 2D is a representative titration curve for a biomolecule suitable for analysis by, for example, the system 110 shown in FIG. 2A. As can be seen in FIG. 2D, application of the negative traveling wave of FIG. 2B urges a biomolecule within the strip 120 to a location in the gel medium of the strip 120 at which the pH of the medium is the same, or substantially so, as the isoelectric point of the biomolecule. In the event the biomolecule is proximate side a of the strip 120, it will be urged toward its isoelectric point in the direction of arrow c upon application of the negative traveling wave of FIG. 2B. And, in the event the biomolecule is proximate side b of the strip 120, it will be urged toward its isoelectric point in the direction of arrow D upon application of the positive traveling wave of FIG. 2C.

The preferred embodiment gel electrophoretic systems may utilize a single voltage controller or multiple voltage controllers. If multiple controllers are used, the controllers may be configured with the electrical grid such that each controller is dedicated to a segment, portion or region of the grid. Or, the controllers can be interfaced with the grid such that each controller is dedicated to particular electrodes, alternatingly arranged over a portion or the entirety of the grid. As described herein, it is preferred that the one or more controllers be configured to generate a wave signal having a polarity opposite from the native charge of the biomolecule to be migrated across a portion of the grid. However, the present invention includes a variety of controller configurations and wave forms for the traveling waves that result in biomolecule transport.

As previously noted, the electrode grids of the present invention systems may be segmented such that a grid includes a plurality of grid segments. Each of the grid segments is physically separate from the other grid segments, however is in electrical communication with one or more controllers or with other segments. The various grid segments may be in electrical communication with other grid segments depending upon the overall system configuration. An example of a multi-segmented grid is shown in FIG. 1A. FIG. 2A illustrates a non-segmented grid.

Although a wide array of configurations, arrangements, and dimensions maybe used for the electrodes and electrode grids described herein, several representative aspects are as follows. The electrode pitch preferably is in the range of from about 600 µm to about 10 µm, and more preferably from about 200 µm to about 40 µm. The spacing between opposing edges of adjacent electrodes is preferably from about 300 µm to about 7.5 µm and more preferably from about 100 µm to about 30 µm. The preferred voltage level applied to the grid and electrodes is from about 5 V to about 0.001 V, and more preferably about 2 V to about 0.10 V. The preferred frequency of the electrical signal depends upon the biomolecules to be migrated, however, frequencies in the range of from about 0.001 to about 10 Hz have been found useful, with preferred frequencies being from about 2 to about 0.020 Hz.

A wide array of commercially available electrophoretic equipment may be modified or retrofitted in accordance with the present invention. Gel electrophoretic systems and cells, IPG strips, power sources, and controllers therefore may be obtained from one or more of the following suppliers: Proteome Systems Limited; Bio-Rad Laboratories; AMRESCO, Inc.; Invitrogen Corp.; Owl Separations Systems; R. Shadel Inc.; Stratagene; Zaxis, Inc.; and Amersham Biosciences.

In general, there is ample opportunity for innovation in the design of specific wave patterns and waveforms to focus, separate, and concentrate proteins and other biomolecules. The implementation of the present invention for a new IEF strategy is a significant advance in the art. Additionally, the present invention provides a new strategy to decrease the time required for an isoelectric focusing operation by utilizing a bidirectional dual traveling wave sweep. Furthermore, by adjusting and selecting a particular frequency for the traveling wave signals, individual focusing efforts may be directed for particular biomolecules. This methodology is particularly attractive for separation attempts of biomolecules having low or "shallow" slopes (with regard to their titration curve) near their isoelectric point.

The present invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A gel electrophoretic system adapted to separate biomolecules according to their isoelectric point, said system comprising:
    an electrophoretic cell having a first end, a second end, and a gel medium extending between said first end and said second end, said gel medium providing a pH gradient along a length dimension of said cell between said first end and said second end;
    an electrode grid disposed in close proximity to said gel including a plurality of closely spaced parallel electrodes extending within a common plane, said grid being oriented with respect to said cell such that said electrodes extend in a direction generally perpendicular to said length dimension of said cell;
    a voltage controller providing a multi-phase electrical signal, wherein said signal is either a positive traveling wave signal or a negative traveling wave signal and opposite from the native charge of the biomolecules to be separated, said controller being in electrical communication with said electrode grid such that said traveling wave signal passes from a first region of said electrode grid to a second region of said electrode grid within the common plane of the grid, thereby separating biomolecules within the common plane;
    wherein said first region of said electrode grid is a first electrode included in said grid, and said second region of said electrode grid is a second electrode included in said grid.

2. The system of claim 1 wherein said second electrode is immediately adjacent to said first electrode.

3. The system of claim 2 wherein said second electrode is separated from said first electrode by at least another electrode included in said grid.

4. A gel electrophoretic system adapted to separate biomolecules according to their isoelectric point, said system comprising:
    an electrophoretic cell having a first end, a second end, and a gel medium extending between said first end and said second end, said gel medium providing a pH gradient along a length dimension of said cell between said first end and said second end;
    an electrode grid disposed in close proximity to said gel including a plurality of closely spaced parallel electrodes extending within a common plane, said grid being oriented with respect to said cell such that said electrodes extend in a direction generally perpendicular to said length dimension of said cell;
    a voltage controller providing a multi-phase electrical signal, wherein said signal is either a positive traveling wave signal or a negative traveling wave signal and opposite from the native charge of the biomolecules to be separated, said controller being in electrical communication with said electrode grid such that said traveling wave signal passes from a first region of said electrode grid to a second region of said electrode grid within the common plane of the grid, thereby separating biomolecules within the common plane;
    wherein said electrode grid comprises:
    a first grid segment; and
    a second grid segment, said second grid segment being physically separate from said first grid segment.

5. A gel electrophoretic system adapted to separate biomolecules according to their isoelectric point, said system comprising:
    an electrophoretic cell having a first end, a second end, and a gel medium extending between said first end and said second end, said gel medium providing a pH gradient along a length dimension of said cell between said first end and said second end;
    an electrode grid disposed in close proximity to said gel including a plurality of closely spaced parallel electrodes extending within, a common plane, said grid being oriented with respect to said cell such that said electrodes extend in a direction generally perpendicular to said length dimension of said cell;
    a voltage controller providing a multi-phase electrical signal, wherein said signal is either a positive traveling wave signal or a negative traveling wave signal and opposite from the native charge of the biomolecules to be separated, said controller being in electrical communication with said electrode grid such that said traveling wave signal passes from a first region of said electrode grid to a second region of said electrode grid within the common plane of the grid, thereby separating biomolecules within the common plane;

a second voltage controller providing a second multi-phase electrical signal, wherein said second signal is either a positive traveling wave signal or a negative traveling wave signal, said second voltage controller being in electrical communication with said electrode grid such that said traveling wave signal passes from a third region of said electrode grid to a fourth region of said electrode grid.

6. The system of claim 5 wherein said electrode grid comprises:
a first grid segment in electrical communication with said voltage controller; and
a second grid segment in electrical communication with said second voltage controller.

7. A process for focusing at least two bands of biomolecules on an immobilized pH gradient (IPG) strip in an electrophoretic system, said system including (i) an electrode grid positioned in close proximity to said strip, said grid having a plurality of closely spaced parallel electrodes, said grid being oriented with respect to said cell such that said electrodes extend generally perpendicular to said strip, (ii) a first voltage controller adapted to provide a first multi-phase electrical signal, said first controller being in electrical communication with at least a portion of said grid, and (iii) a second voltage controller adapted to provide a second multi-phase electrical signal, said second controller being in electrical communication with at least another portion of said grid, said process comprising:
identifying the native charge of biomolecules in a first band disposed closest to a first end of said strip;
identifying the native charge of biomolecules in a second band disposed closest to a second end of said strip;
operating said first voltage controller to generate said first multi-phase electrical signal and cause said first signal to pass from said first end of said strip toward said second end of said strip, wherein said first signal has a polarity opposite from said native charge of said biomolecules in said first band; and
operating said second voltage controller to generate said second multi-phase electrical signal and cause said second signal to pass from said second end of said strip toward said first end of said strip, wherein said second signal has a polarity opposite from said native charge of said biomolecules in said second band.

8. A gel electrophoretic system adapted to separate biomolecules according to their isoelectric point, said system comprising:
an electrophoretic cell having a first end, a second end, and a gel medium extending between said first end and said second end, said gel medium providing a pH gradient along a length dimension of said cell between said first end and said second end;
an electrode grid disposed in close proximity to said gel including a plurality of closely spaced parallel electrodes extending within a common plane, said grid being oriented with respect to said cell such that said electrodes extend in a direction generally perpendicular to said length dimension of said cell;
a voltage controller providing a multi-phase electrical signal, wherein said signal is either a positive traveling wave signal or a negative traveling wave signal and opposite from the native charge of the biomolecules to be separated, said controller being in electrical communication with said electrode grid such that said traveling wave signal passes from a first region of said electrode grid to a second region of said electrode grid within the common plane of the grid, thereby separating biomolecules within the common plane;
wherein the voltage controller provides the electrical signal at a frequency of from about 2 to about 0.020 Hz.

9. A gel electrophoretic system for decreasing the time required for conducting isoelectric focusing of a sample of biomolecules, said system comprising:
an immobilized pH gradient (IPG) strip, said strip providing a medium with a pH increasing along a longitudinal axis of said strip;
an electrode grid disposed adjacent to said strip, said electrode grid including a plurality of parallel electrodes, said electrodes extending in a direction generally transverse to said longitudinal axis of said strip;
a first voltage controller providing a multi-phase electrical signal in the form of either a positive traveling wave signal or a negative traveling wave signal, the polarity being opposite from the native charge of the biomolecules to be isoelectrically focused, said first voltage controller being in electrical communication with said electrode grid such that said traveling wave signal travels from a first region of said electrode grid to a second region of said electrode grid;
wherein the first voltage controller provides the electrical signal at a frequency of from about 2 to about 0.020 Hz.

* * * * *